(12) United States Patent
Alkhagen et al.

(10) Patent No.: US 8,901,368 B2
(45) Date of Patent: Dec. 2, 2014

(54) ABSORBENT CORE COMPRISING MULTIPLE SUBLAYERS

(75) Inventors: Mårten Alkhagen, Mölndal (SE); Anna Bagger-Sjöbäck, Göteborg (SE); Bertil Olandersson, Mölnlycke (SE)

(73) Assignee: SCA Hygiene Products AB, Göteborg (SE)

( * ) Notice: Subject to any disclaimer, the term of this patent is extended or adjusted under 35 U.S.C. 154(b) by 611 days.

(21) Appl. No.: 12/743,260

(22) PCT Filed: Dec. 7, 2007

(86) PCT No.: PCT/SE2007/050952
§ 371 (c)(1), (2), (4) Date: May 17, 2010

(87) PCT Pub. No.: WO2009/072947
PCT Pub. Date: Jun. 11, 2009

(65) Prior Publication Data
US 2010/0249739 A1    Sep. 30, 2010

(51) Int. Cl.
A61F 13/15 (2006.01)
A61F 13/20 (2006.01)
A61L 15/60 (2006.01)
A61F 13/53 (2006.01)

(52) U.S. Cl.
CPC *A61L 15/60* (2013.01); *A61F 13/53* (2013.01)
USPC ........................................................ 604/367

(58) Field of Classification Search
USPC ............. 604/358, 367, 374–375, 378, 385.01
See application file for complete search history.

(56) References Cited

U.S. PATENT DOCUMENTS 4,102,340 A * 7/1978 Mesek et al. .................. 604/368
4,610,678 A    9/1986 Weisman et al.
(Continued)

FOREIGN PATENT DOCUMENTS

CN    1067180 A    12/1992
CN    1620275 A    5/2005
(Continued)

OTHER PUBLICATIONS

International Search Report for PCT/SE2007/050952, mailed Sep. 25, 2008.
(Continued)

*Primary Examiner* — Michele M Kidwell
(74) *Attorney, Agent, or Firm* — Buchanan Ingersoll & Rooney PC

(57) ABSTRACT

An absorbent core for use in an absorbent product, such as a sanitary napkin, a diaper, an incontinence protection or the like. The core after compression has a material density (based on the total content of the core) of at least 200 kg/m$^3$, preferably at least 230 kg/m$^3$, measured at a pressure of 0.5 kPa. The absorbent core has been formed in-line as a discrete or continuous core and includes SAP-particles, where at least 99.5% of the SAP-particles have a size of maximally 600 µm. Hereby, problems with regard to clogging of SAP-particles to compression rollers during manufacturing are markedly reduced. Further, a method for manufacturing the absorbent core, as well as an absorbent product including the absorbent core is described.

20 Claims, 5 Drawing Sheets

(56) References Cited

U.S. PATENT DOCUMENTS

| | | | |
|---|---|---|---|
| 4,724,114 A | 2/1988 | McFarland et al. | |
| 5,419,956 A | 5/1995 | Roe | |
| 5,422,169 A * | 6/1995 | Roe | 428/212 |
| 5,866,242 A | 2/1999 | Tan et al. | |
| 5,961,506 A * | 10/1999 | Guidotti et al. | 604/378 |
| 6,124,391 A | 9/2000 | Sun et al. | |
| 6,494,871 B1 | 12/2002 | Lariviere et al. | |
| 6,579,272 B1 | 6/2003 | Samuelsson et al. | |
| 2002/0115971 A1* | 8/2002 | Holmes et al. | 604/378 |
| 2002/0156441 A1 | 10/2002 | Sawyer et al. | |
| 2004/0243078 A1 | 12/2004 | Guidotti et al. | |
| 2005/0165374 A1* | 7/2005 | Karlsson et al. | 604/368 |
| 2006/0004336 A1 | 1/2006 | Zhang et al. | |

FOREIGN PATENT DOCUMENTS

| | | |
|---|---|---|
| CN | 1976729 A | 6/2007 |
| EP | 0 956 844 A2 | 11/1999 |
| EP | 1 427 658 B1 | 6/2006 |
| WO | WO 92/18171 A1 | 10/1992 |
| WO | WO 94/07547 A1 | 4/1994 |
| WO | WO 94/10956 A1 | 5/1994 |
| WO | WO 00/10619 A1 | 3/2000 |
| WO | WO 02/49565 A2 | 6/2002 |
| WO | WO 02/085269 A1 | 10/2002 |
| WO | WO 02/085270 A1 | 10/2002 |
| WO | WO 02/087483 A1 | 11/2002 |
| WO | WO 02/087484 A1 | 11/2002 |
| WO | 03047486 A1 | 6/2003 |
| WO | WO 03/047484 A1 | 6/2003 |
| WO | WO 03/053301 A1 | 7/2003 |
| WO | WO 03/059222 A1 | 7/2003 |
| WO | WO 2004/049989 A1 | 6/2004 |
| WO | WO 2004/084784 A1 | 10/2004 |
| WO | WO 2007/111873 A2 | 10/2007 |

OTHER PUBLICATIONS

Australian Examination Report dated Apr. 16, 2013 issued in the corresponding Australian Patent Application No. 2007362082.

Colombian Official Action dated Jan. 22, 2013 issued in the corresponding Colombian Patent Application No. 10-67251-8 and partial English-language translation.

Chinese Office Action dated Jul. 1, 2013 issued in the corresponding Chinese Patent Application No. 200780101706.5 and English language translation (17 pages).

European Communication dated May 23, 2013 issued in the corresponding European Patent Application No. 07 852 224.0—1455.

* cited by examiner

ABSORBENT CORE COMPRISING MULTIPLE SUBLAYERS

TECHNICAL FIELD

The invention refers to an absorbent core for use in an absorbent product, such as a sanitary napkin, a diaper, an incontinence protection or the like, the core after compression having a material density (based on the total content of the core) of at least 200 kg/m3, preferably at least 230 kg/m3, measured at a pressure of 0.5 kPa, whereby the absorbent core has been formed in-line as a discrete or continuous core. Also, the invention refers to an absorbent product comprising the absorbent core of the invention as well as a method for manufacturing the absorbent core.

BACKGROUND OF THE INVENTION

In order to meet demands from customers as well as for manufacturing purposes it has become increasingly important to provide sanitary napkins being as small and thin as possible, but still having advantageous absorbent properties. In order to provide such absorbent products, the absorbent layer of the product is often compressed before or during manufacture of the product.

Conventionally, the absorbent layer of thin sanitary napkins are provided in the form of a pre-compressed material roll, whereby the roll is cut to pieces of a suitable size, and the pieces are put into the absorbent product during manufacturing of the product. Such pre-compressed material in the form of a roll is normally expensive to provide, because of the need for external supply and a complex handling and manufacturing, due to e.g. the need of cutting unnecessary material during manufacturing, which also results in waste material. Thus, it would be beneficial if the formation and/or compression could be performed during manufacturing of the product.

The absorbent core(s), typically comprising one or more absorbent layer(s), normally comprises SAP-material, often consisting of particles having varying sizes, and typically a largest diameter size of about 850 µm. A problem in the art is that when an absorbent core or layer comprising SAP particles is compressed (whereby a compression roller having a distance between the rollers of typically about 250 µm is used) the SAP particles tend to clog to the compression rollers, thereby causing rupture of the core resulting in manufacturing process arrests. This is especially a problem in the field of absorbent products, wherein many individual products need to be produced in a short time using high manufacturing rates, and is normally not acceptable, not the least for cost reasons to and/or quality aspects. Partly, this problem appears to be a result of deformation or rupture of the SAP-particles, resulting in stickiness of the particles and as a result clogging to the compression rollers. This problem is even more often encountered in environments or in weather conditions having high air humidity, as is often the case e.g. during summer time in many areas.

One way to accomplish compression of a SAP-containing absorbent core without a resulting clogging, can be to provide a protection of tissue or nonwoven covering the SAP-particles. However, these materials are normally expensive, and the tissue material, for instance, typically has rather weak absorption properties. Also, using a covering sheet is complicated from a process point of view, since the edges of the covering material typically need to be cut, so that the tissue material does not extend outside the product sealing, which could result in leakage problems during use of the product.

From the prior art, WO00/10619, an absorbent product is disclosed comprising superabsorbent particles having anti-caking properties, in order to prevent the particles to adhere to manufacturing equipment. The anti-caking properties are provided by mixing SAP with inorganic powder, e.g. clay. However, these particles have not been used in connection with high density compression rollers.

Accordingly, there is a need in the art for an improved manufacturing process for manufacturing absorbent cores, thereby limiting the drawbacks and problems mentioned above, especially with regard to clogging of SAP-particles to compression rollers during manufacturing.

Thus, one object of the invention is to provide an absorbent core for use in an absorbent product, which core is compressed during manufacturing, and can be provided in a simpler and/or less expensive way than today, and which core further has absorbent properties that are acceptable and/or beneficial.

SUMMARY OF THE INVENTION

In a first aspect of the present invention this object is advantageously met by an absorbent core according to the invention. Especially, it was found by the inventors that by using SAP-particles having a largest size smaller than the conventional size (which is about 850 µm), the clogging problems were drastically reduced and in some cases almost completely avoided. Also, the absorbent properties of a product manufactured in this way were surprisingly of the same level as a conventional product, with regard to e.g. rewetting and liquid inlet properties.

Also, in a second aspect of the invention, a method for manufacturing an absorbent core is provided.

Another advantage obtained by the present invention is that by using smaller SAP-particles, a better distribution of SAP-particles is obtained in the core. Further, smaller SAP-particles tend to better mixed with the other material of the core. Also, by using smaller SAP-particles, less contamination and waste are expected around the manufacturing facilities, since larger particles more easily are slung out.

Moreover, air moisture is normally a very critical parameter with regard to clogging of SAP particles during compression and manufacturing, resulting in seasonal variations and geographical concerns when planning production of absorbent products comprising SAP. These concerns can be limited and/or avoided by manufacturing an absorbent core in accordance with the invention. Further, a high level of air moisture is typically beneficial in order to achieve an even formation of pulp (that is less static) that normally is easier to compress hard. Thus, by manufacturing an absorbent core in accordance with the invention, thereby reducing the clogging problem, the manufacturing can be performed at higher air moisture levels, thereby achieving the benefits of using a higher air moisture level.

Further, by manufacturing an absorbent core in accordance with the invention the compressing rollers that are used do not need to be warm, which is common in conventional manufacturing. Using heated rollers is an alternative way to reduce clogging of SAP-particles. However, it can be technically difficult (e.g. due to vacuum properties), expensive and time-consuming, and therefore it is desirable to avoid the use of warm rollers, which is fully possible by using the present invention.

In a third aspect the invention refers to an absorbent product, chosen from a sanitary napkin, a diaper, or an incontinence protection, comprising the absorbent core of the invention.

Moreover, since the smaller SAP-particles that are used have a larger total surface area (compared to larger SAP-particles), it has been shown that the absorbent core of the invention is suitable for absorption of menstrual fluids. Thus, in a second aspect the invention refers to the use of an absorbent core for absorbing menstrual fluids.

DEFINITIONS

By a "thin" sanitary napkin is meant a sanitary napkin wherein at least part of the absorbent core is thinner than 3 mm, preferably thinner than 2 mm, more preferably thinner than 1.5 mm.

By a "longitudinal" direction or "machine direction" is meant the direction along the length of the absorbent product, i.e. from the rear to the front of the product (or vice versa), and by "lateral" direction or "cross-direction" is meant the direction from side edge to side edge of the product, i.e. across the width of the product.

By "clogging" of SAP-particles to compression rollers is meant that the SAP-particles adheres to the compression rollers, because of e.g. sticky surface properties of the SAP particles and/or other means of interaction between the SAP-particles and the compression rollers.

By "the absorbent core has been formed in-line as a discrete or continuous core" is meant that the core is formed during manufacturing, e.g. on a conveyor belt, either as a discrete core formed by e.g. air-laying fluff pulp on a mat former, or that the absorbent core is formed as continuous layer (or layers), that is cut to discrete units during manufacturing, e.g. on the conveyor belt.

By "size" of SAP-particles is meant the largest diameter size, i.e. the size determined by screening according to ERT420.2-02 (particle size distribution).

By a core being "compressed during manufacturing" is meant that the core is compressed during assembling of the absorbent product, including compression of the core, assembling of top sheet, absorbent core and back sheet etc.

A number of methods for measuring the "density" of absorbent cores, or the average density of samples, have been described in the literature. In particular, the average density of a sample of absorbent core may be measured according to the following procedure:

The absorbent article is carefully delaminated: any inner or outer coversheets are removed so as to only leave a unitary core.

A pressure of 0.5 kPa is applied to the absorbent core via a foot which corresponds in area to the area of the sample of absorbent core for which the density is to be measured The thickness of the sample is measured while subject to this pressure.

The samples for which densities are to be calculated are cut out from the core, and the surface weight (g/cm$^2$) of these samples is calculated from their mass/surface area.

From the surface weight and the thickness, the average density of these areas is calculated. The average density (kg/m$^3$) is calculated by dividing the surface weight by the thickness.

DETAILED DESCRIPTION OF THE INVENTION

Figure 1:
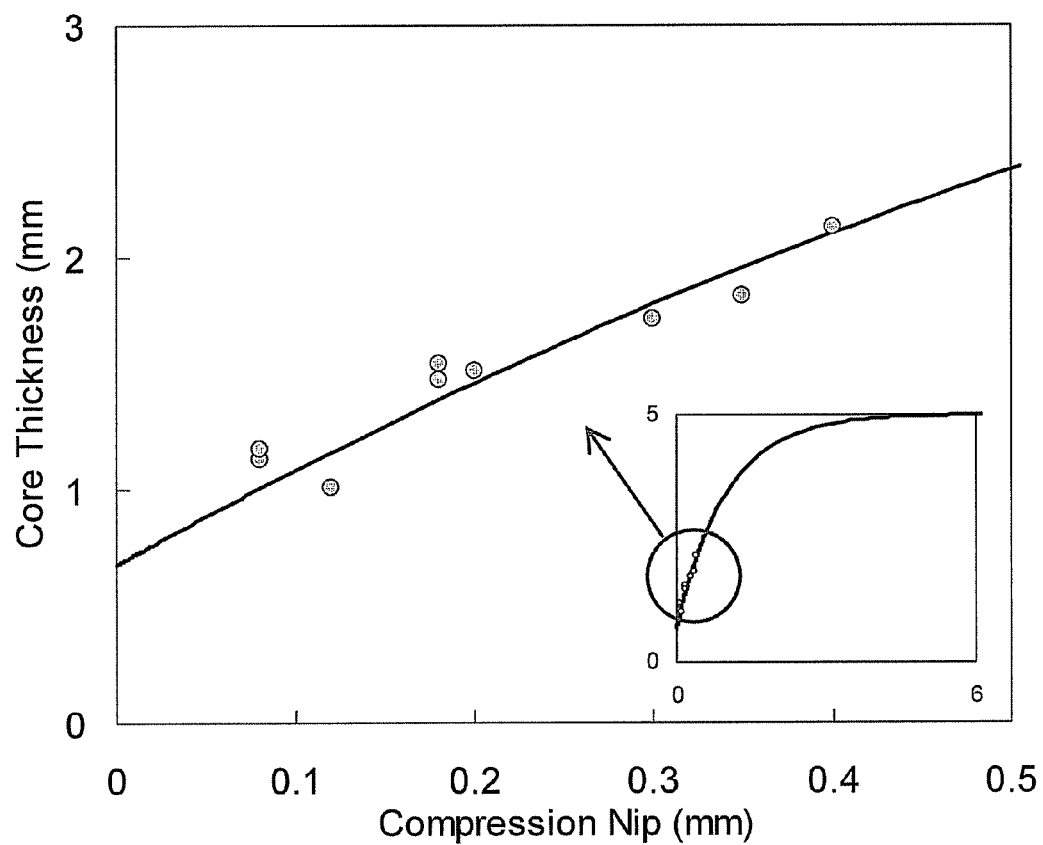
FIG. 1. The core thickness dependence on the compression nip distance, the circles indicate measured data and the solid line is a fitted function.

In a first aspect, the invention refers to an absorbent core for use in an absorbent product, such as a sanitary napkin, a diaper, an incontinence protection or the like, the core after compression having a material density (based on the total content of the core) of at least 200 kg/m3, preferably at least 230 kg/m3, measured at a pressure of 0.5 kPa, whereby the absorbent core has been formed in-line as a discrete or continuous core, characterised by that the absorbent core comprises SAP-particles, whereby at least 99.5% of the SAP-particles have a size of maximally 600 μm.

Hereby, since smaller SAP-particles is used compared to a conventional absorbent core, is the risk for clogging is strongly reduced, as shown e.g. by the appended examples.

In one embodiment, at least 99.5% of the SAP-particles have a size of maximally 550 μm, preferably of maximally 400 μm, more preferably of maximally 350 μm, and most preferably of maximally 300 μm. Hereby, the risk for clogging is even further reduced.

The absorbent core is typically built up by one or more layers of defibrillated cellulose fibres, for example cellulose fluff pulp. Other materials, which may be used, are for example absorbing or wettable nonwoven material, foam material, synthetic fibre materials or peat. In addition to cellulose fibres or other absorbing materials, the absorbent core comprises superabsorbent material, so called SAP (super absorbent polymers), that is material in the form of fibres, particles, granula, film or the like, which material has the ability to absorb fluid corresponding to several times the weight of the superabsorbent material. The superabsorbent material binds the fluid and foams a fluid-containing gel. Moreover, the absorbent core may comprise binders, form-stabilising components or the like. The absorbent core may be chemically or physically treated in order to change the absorption properties. In accordance with the present invention, an absorbent layer with compressed regions and/or being compressed in the entire layer(s) is provided in order to control the fluid flow in the absorbent body. It is also possible to enclose the absorbent layer(s) in an envelope of for example tissue material. In the prior art, it is common to use tissue material in the absorbent core or in e.g. distribution layers. However, this can be disadvantageous for absorption of e.g. menstrual fluid and/or urine, since the tissue material tends to bind to the structure. Tissue has typically a dense structure which results in a slower absorption and more distribution of the fluid. Further, the use of tissue results in a more expensive and more complex process. Hence, in the present invention it is preferable to use other materials than tissue for the absorbent core.

The absorbent core can be arranged in several different ways as long as proper absorbent properties are achieved. In one embodiment, the absorbent core comprises at least three sub-layers, wherein a first sub-layer, viewed from the wearer-facing side of the core, primarily comprises pulp, the second sub-layer comprises the SAP-particles and pulp, and the third sub-layer primarily comprises pulp.

In another embodiment, the amount of SAP in the absorbent core is in the interval from 5 to 60%-weight of the absorbent core, preferably 10 to 50%-weight, based on the total weight of the core.

Superabsorbent polymers are water-swellable, water-insoluble organic or inorganic materials capable of absorbing at least about 20 times their own weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, etc. possesses a higher crosslink density than the inner portion of the superabsorbent. Naturally, also other material combinations known in the art may be considered, and are thus included in the scope of the invention.

Typically, the absorbent core has in its longitudinal direction an outstretched form, and may for example be essentially rectangular, T-shaped or hourglass-shaped. An hourglass-shaped absorbent core is wider in the front and rear parts than in the crotch part, in order to provide an efficient fluid absorption simultaneously as the design facilitates the product to form and to close around the user, thereby giving a better fit around the legs (see e.g. WO 03/053301, EP 0 956 844, WO 03/047484, WO 02/087484, WO 02/085270, WO 03/059222, WO 02/087483, WO 02/085269 and related applications, which describe absorbent products which comprise a stiffening element that is intended to contribute to the three-dimensional shape of the products during their use). Also, the absorbent core can be designed in a more complex form, so that comfort, fitting, or absorption properties are optimised. In a preferred embodiment of the present invention, the absorbent core has essentially straight and parallel longitudinal edges. The rear and front edges are rounded in order to fit the shape of the product.

The absorbent core can be provided in the form of a roll-material or a festooned material, whereby the material typically is provided with a high compression, or the structure can be formed by means of air-laying technique whereby it is compressed during manufacturing of the product. The latter choice is preferred in the context of the present invention, since material waste is reduced using mat formation compared to a roll material that needs to be cut. An alternative to this is to dry-form a pulp mat, such as described in WO94/10956.

In a second aspect the invention refers to a method for manufacturing an absorbent core according to the invention, comprising the steps of:
(a) forming an absorbent core in-line as a discrete or continuous core, wherein the core comprises SAP-particles so that at least 99.5% of the SAP-particles have a size of maximally 600 µm;
(b) compressing the absorbent core between compressing rollers so that the core after compression has a material density (based on the total content of the core) of at least 200 kg/m3, preferably at least 230 kg/m3, measured at a pressure of 0.5 kPa;
(c) (optionally) providing a top sheet and a back sheet after compression, positioning the absorbent core between the top sheet and the back sheet, and sealing the product in order to provide a finished absorbent article.

The absorbent core of the invention is preferably formed in-line in a form, meaning that the layers of the invention are provided by way of air-laying technique by supplying e.g fluff pulp to a mat former or the like and shaping the material to the desired shape.

The compression of the absorbent core can be obtained by any means. However, it is preferable to use a process referred to as high density compression (HDC) as further outlined in EP-B-1427658, which document hereby is included as a reference.

Thus, in another embodiment, the compression of the absorbent core is performed by way of HDC (high density core). For example, the compression of the absorbent core can be performed in two-three steps, involving a pre-compression and thereafter compression of the core in one or two steps.

For example, to start with a pre-compression of the core material is performed using typically a distance between rollers of about 600-800 µm, in order to press out air that is contained in the material, so that the product does not get stuck to perforations of the compression rollers during compression. Thereafter, two consecutive compression steps are performed. In a first compression step, a distance between the rollers of about 250 µm is typically used, whereby the outer part of the absorbent core is compressed. In a second compression step, typically using a distance between the rollers of about 250 µm, the central part of the absorbent core is compressed. For example, the absorbent core is fed on a conveying track passing two compression rollers, each compressing the right and left outer parts of the absorbent core (seen in the longitudinal direction) in the first compression step, and thereafter passing a single compression roller compressing the central part of the absorbent core in a second compression step, so that the entire absorbent core is compressed as a result of the two consecutive compression steps. See also EP-B-1427658 for further details.

After compression of the absorbent layer, the absorbent product is typically manufactured by providing the additional components, i.e. the back sheet, the top sheet as well as any other components, which are put together at a conveying track, and finally packaged in a package for the absorbent product.

Advantageously, the compressed absorbent core(s) can be supplied directly to the process line for manufacturing the absorbent product, which however requires that the feed speed of the process line for the absorbent product and the feed speed of the absorbent core compression are synchronous.

In one embodiment, the manufacturing rate of the absorbent core at one line is at least 300, preferably at least 350, more preferably at least 400, even more preferably at least 500 in/min.

Also, (in case a complex or non-rectangular shaped core is desired) by manufacturing an absorbent core in accordance with the invention, thereby avoiding the use of e.g. an absorbent core that is provided in the form of a pre-compressed roll material, material waste can be reduced or eliminated, since cutting of absorbent core material that extends outside the desired or intended core shape, thereby having the potential to give rise to leakage during use, or decreased fit or visual appearance, can be avoided. Hence, material waste can be reduced. For example, for a complex core (see e.g. WO 03/053301, EP 0 956 844, WO 03/047484, WO 02/087484, WO 02/085270, WO 03/059222, WO 02/087483, WO 02/085269 and related applications, which describe absorbent products which comprise a stiffening element that is intended to contribute to the three-dimensional shape of the products during their use) about 40% of the material waste can be reduced.

Still further, by using a smaller SAP-particle waste of SAP-particles per product can be reduced during manufacturing. Thus, in one further embodiment, SAP-waste per product during manufacturing is reduced.

In a third aspect the invention refers to an absorbent product, chosen from a sanitary napkin, a diaper, or an incontinence protection, comprising a top sheet, a back sheet and an absorbent core according to the invention between the top sheet and the back sheet.

Typically, an absorbent product of the invention is designed as follows: Starting from the top (intended to be closest to the skin of the wearer at use) optional textile-like edges can be positioned, which, if used, are positioned at the longitudinal edges of the top sheet. Beneath the top sheet an optional liquid distribution layer can be positioned. In a preferred embodiment the liquid distribution layer is a high loft layer or a low density airlaid. Beneath the liquid distribution layer, or directly beneath the top sheet (in case no liquid distribution layer is present), the absorbent core is positioned. For example, the absorbent core is a pressure-bonded airlaid core comprising superabsorbent polymers. In a preferred embodiment, in order to provide a high absorption capacity, the absorbent core comprises about 5-60% SAP. Beneath the core structure, a back sheet is provided. For example, the back sheet is a plastic film. At the outside of the back sheet a release paper is optionally positioned which is fastened to the back sheet e.g. by glue strings or by any other conventional means. An edge sealing, binding the optional textile edges, the liquid distribution layer and the back sheet at the longitudinal edges can also be positioned.

The liquid-permeable top sheet is preferably made of a material showing properties like dryness and softness at use of the absorbent product, as this sheet lies against the body of the wearer. It is normally desired, that the sheet has a soft and textile-like surface, which remains dry also at repeated wettings. The top sheet may for example be composed of nonwoven material with a soft and smooth surface, such as for example a spunbond made of polypropylene fibres. Other examples of material in the top sheet may for example be perforated plastic films, such as for example a polyethylene film. The top sheet may be connected to the underlying back sheet and to the absorption core by, for example, glue, ultrasonic bonding or through some kind of thermal bonding.

The liquid-impermeable back sheet consists of a flexible material, preferably a thin plastic film of PE (polyethylene), PP (polypropylene), a polyester, or some other kind of suitable material, such as a hydrophobic nonwoven-layer or a laminate of a thin film and a nonwoven material. These types of laminates are often used in order to achieve a soft and a textile-like surface of the back sheet. In order to accomplish an airier and comfortable product it is also possible to use breathable back sheets, which prevents fluid from coming out of the absorbent product, but that allows moisture to be ventilated. These breathable back sheets may be composed of single material layers, or of laminates of, for example, blown or moulded polyethylene films, which have been laminated with, for example, a nonwoven layer of spunbond or of spunbond-meltblown-spunbond (SMS).

Additional liquid distribution layers may be used in the product of the invention, preferably between the absorbent structure and the top sheet. For instance, additional layers improving the properties may be used, such as a transfer layer or various types of fluid-spreading material layers or inserts, so called waddings or high-loft layers. Typically, the liquid distribution layer is a porous, resilient, relatively thick material layer, for example in the form of a fibrous high loft layer, a carded fibrous web, a tow material or other type of bulky and resilient fibrous material having a high momentaneous liquid receiving capacity and which can temporarily store liquid before it is absorbed by the underlying absorbent core. Also, the liquid distribution layer may be in the form of a porous foam material. Also, it may consist of two or more material layers, or of low density airlaid.

Further, the product of the invention is typically equipped with a release paper or plastic film that partly or totally covers the outer side of the back sheet of the product. The release paper is fastened to the back sheet by means of glue strings.

At the periphery of the product, with a width of e.g. about 0.5-1.5 cm, an edge sealing is provided in order to secure the top sheet, the back sheet and optionally the liquid distribution layer to each other. The edge sealing can be made by means of adhering the layers to each other, by means of embossment, by means of heat welding, by means of ultra sonic bonding, by means of glue or a combination of these methods.

In order to prevent fluid to leak out, the absorbent product on the side that is facing the wearer may also be equipped with inner fluid barriers, which are attached in connection to the longitudinal edges.

Further, the product of the invention may be equipped with wings. Also products equipped with other layers than described in this disclosure are also included in the scope of the invention.

The product can be hour-glass shaped (wherein the rear part and front part are essentially equally wide measured in the cross-direction, and the crotch part is less wide than the front or rear part) or it can be asymmetrically shaped or it can have any other shape that is appropriate for products of this type. By asymmetrical can be meant that the product is least wide in the crotch part of the product (measured in cross-direction) and it is wider in the front part than in the rear part (measured at the widest position of the rear and front part respectively in cross-direction), in order to provide an improved fit for the wearer.

Another example of asymmetry is the complex shaped core as disclosed in e.g. WO 03/053301, EP 0 956 844, WO 03/047484, WO 02/087484, WO 02/085270, WO 03/059222, WO 02/087483, WO 02/085269 and related applications, which describe absorbent products which comprise a stiffening element that is intended to contribute to the three-dimensional shape of the products during their use.

During manufacturing, the absorbent product, as well as its various layers, can be positioned on the conveyor belt so that the longitudinal direction of the product (or its layers) is positioned in the direction of movement of the conveyor belt, or orthogonally to the direction of movement of the conveyor belt.

The various aspects and embodiments of the invention can of course be modified within the scope of the invention. In order to further illustrate the invention, the following examples are provided, which however not should be interpreted as narrowing the intended scope of protection as defined by the appended claims.

EXAMPLES

Example 1

An Evaluation of how the Sap Amount and the Degree of Core Compression Influence the Processability The test plan was designed as a full-scale test with three levels of SAP (BASF HySorb M-7055) amounts and three levels of absorption core compressions. The cores were produced in a conventional converting machine at a line speed of 300 m/min and were compressed in-line with a high density compression unit. The measured parameters were resulting core thickness measured at a pressure of 0.5 kPa and amount of defect or missing cores due to clogging to the compression rollers. To count the defect cores, an in-line vision system measuring transmitted light was used. The vision system analyses each core in real time, and cores with a surface area and/or length less than 80% of the specified dimensions were counted as defect cores (300 m/min in this case, and every core was identified).

By plotting the measured core thickness data versus the core compression nip it is obvious that there is a close correlation between those. This is of course expected to the skilled man in the art; however the data also indicates that the amount of SAP does not have a strong influence in the tested range (0.15-1.00 g SAP and 2.2 g pulp fibres), cf. FIG. 1.

To predict the amount of clogging in the high density compression unit (measured as defect cores by a vision system as described above) it is possible to conduct a theoretical argument as follows: The clogging should be proportional to the probability that there is a SAP granular in the compression nip and to the compression energy or violence. From a pure geometrical standpoint it is easily conceived that the probability to find SAP in the line of compression must be proportional to the line density of SAP which in its turn is proportional to the square root of the SAP weight of one core, $m_{SAP}$. The energy relation is estimated as proportional to the inverse of the compression gap, $t_{nip}$. This approximation is at least correct when the core gap is close to or exactly zero as the inverse then becomes infinite. Now it is possible to postulate a SAP intensity function which should be proportional to the amount of defect cores:

$$I_{SAP} = \frac{\sqrt{m_{SAP}}}{t_{nip}}.$$

Figure 2:
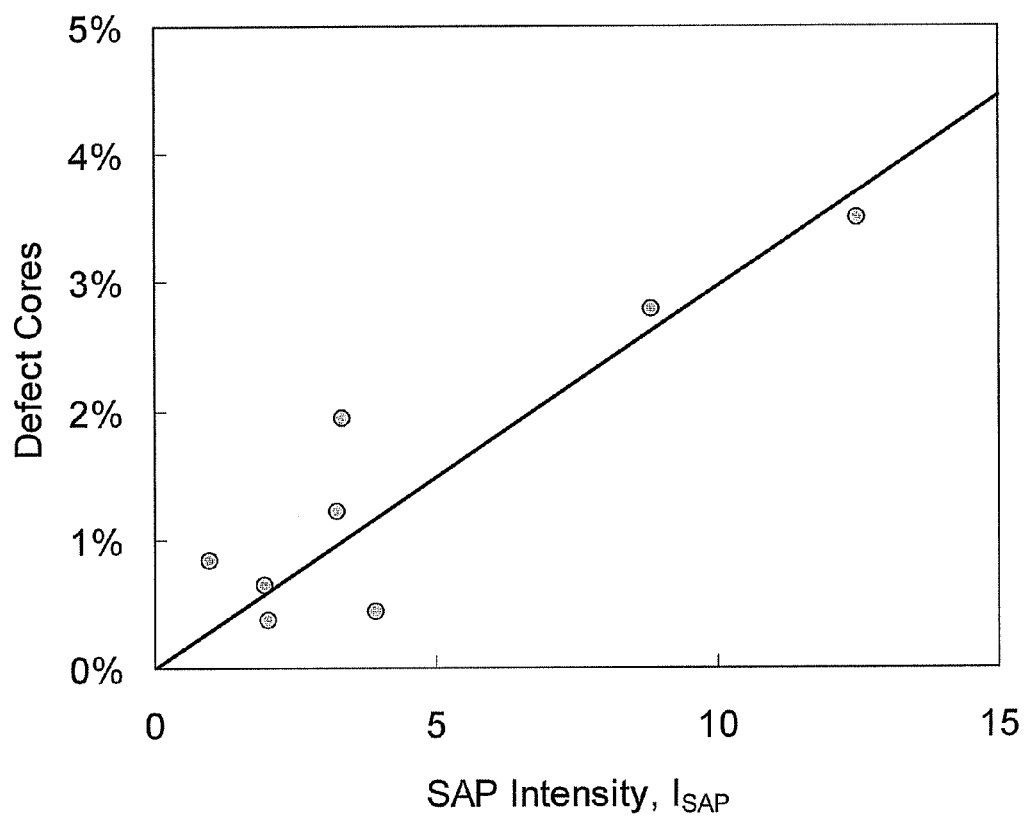
FIG. 2. The dependence of the amount of defect cores on the SAP intensity in the compression nip, the circles indicate measured data and the solid line is a fitted function (linear regression).

In FIG. 2 the amount of defect cores is plotted against the above defined SAP intensity function and the correlation is quite good. The slope of the fitted line in FIG. 2 is only valid for the conditions during the tests; in general the slope should be dependent of:
  Outer factors such as the roller surface properties, the air humidity, the temperature, the peripheral velocity.
  The core design including amount of pulp fibres, type of pulp, precompression, core forming evenness, core shape, quality of SAP-free layers.
  The SAP properties such as mechanical properties, moisture content, size distribution, surface treatment, shape of the granules, batch.

Example 2

An Evaluation of how the Sap Properties Influence the Amount of Defect Cores

Figure 3:
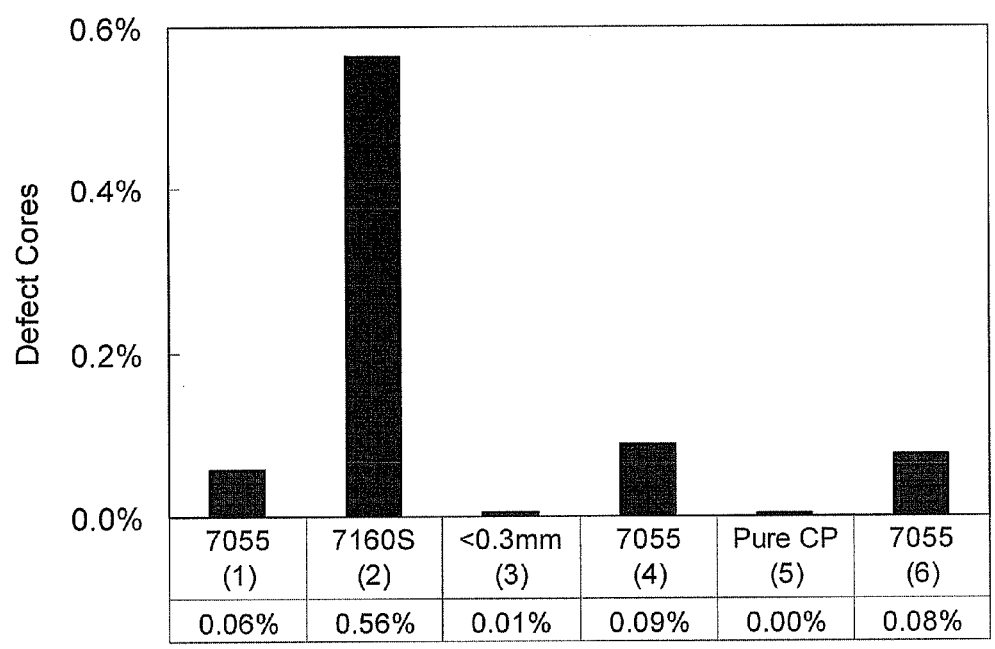
FIG. 3. The dependence of the amount of defect cores on different SAP grades.

To evaluate how the SAP properties influences the amount of defect cores due to clogging of the compression rollers three different SAP grades were tested. The different SAP grades are presented in Table 1, wherein "7160" refers to a standard SAP, and "7160S" refers to an anti-caking SAP (surface treated). The cores were produced in a standard converting machine at a line speed of 300 m/min and the cores had an upper and a lower layer of pure pulp with a basis weight of approximately 85 g/m² each and a middle layer of pulp with a basis weight of approximately 85 g/m² and SAP with a basis weight of approximately 50 g/m². The amount of defect cores was counted by means of a vision system, cf. Example 1, during production of approximately 30000 cores per experiment. The amount of defect cores per SAP grade is plotted in FIG. 3. From FIG. 3 it is clear that the experiment with cores with pure pulp fibres and without SAP gives a close to zero amount of defect cores. It is also clear that the experiment with fine SAP (BASF LuquaSorb 1030) particles also gives a close to zero amount of defect cores. The experiments with the standard SAP (BASF HySorb B-7160) give a significantly worse result compared with the fine SAP grade. Furthermore the repeatability of the experiments is confirmed with the repeated experiments with the standard SAP, BASF 7160. Obviously there is no advantage of using a surface treated standard SAP (BASF HySorb M-7160S). A positive side effect of using the fine SAP was that the SAP distribution, as measured by the vision system, in the cores became more even compared with the standard SAP cores.

TABLE 1

| SAP grade (BASF) | Average diameter (μm) |
| --- | --- |
| HySorb B-7160 | 45-850 (99%) |
| HySorb M-7160S | 45-850 (99%) |
| LuquaSorb 1030 | <300 |

Example 3

SAP Contamination of the Production Machine

Figure 4:
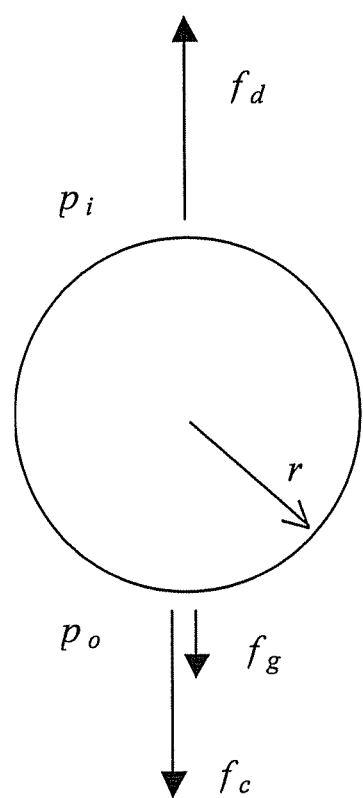
FIG. 4. Forces acting on a SAP particle where $f_d$=the drag force, $f_g$=the gravity force, $f_e$=the centrifugal force, $p_i$=the inner air pressure at the particle, $p_o$=the outer air pressure at the particle, and r=the particle radius.
Figure 5:
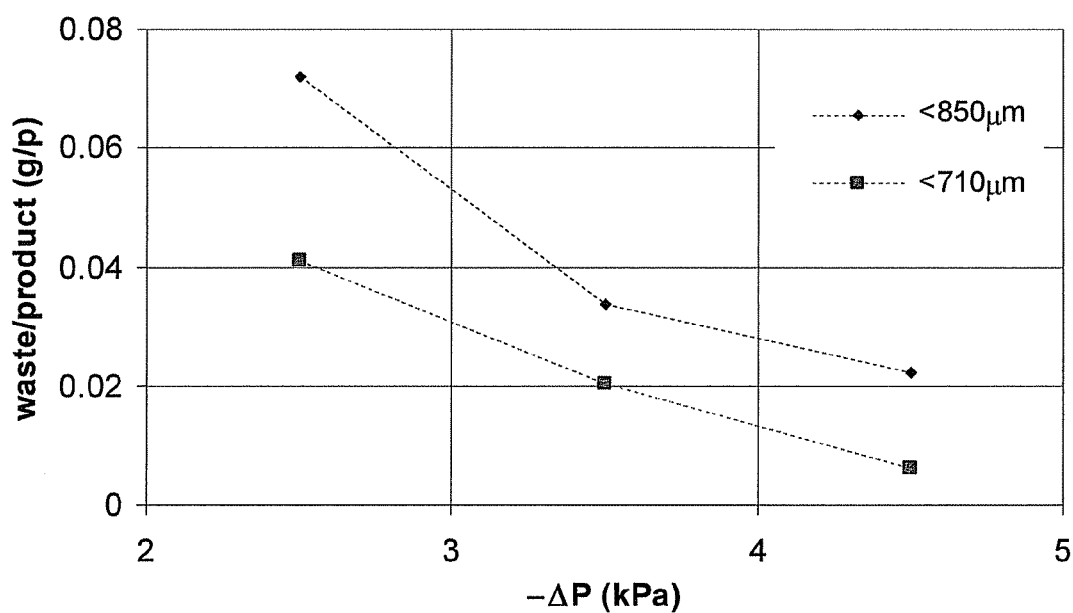
FIG. 5. The SAP waste dependence on the pressure gradient over the mat formed core for two different SAP particle maximum diameters.

When the produced cores are transported via suction drums there is always a risk of SAP particles spilling out of the cores, resulting in an unwanted contamination of the production machine and unwanted waste of SAP. For the skilled man in the art there is an obvious force balance acting on the SAP particles, cf. FIG. 4 where the positive forces, repulsing the particle, are the gravitational and centrifugal forces, and the negative forces, holding the particle, are the drag force and the pressure gradient force. 4 is valid for the worst case where the gravitational and the centrifugal forces are concurrent. The centrifugal force is dependent of the peripheral velocity of the suction drum and the drag force is dependent of the air velocity through the core, which is related to the core pressure gradient. To evaluate the effect of the different forces the core pressure gradient were varied (by adjusting the rpm of the suction fan). As is obvious for the skilled man in the art, all forces are also related to the size and density of the particles. From theoretical analyses the smaller and/or less dense the particle is the easier it is to hold it in the core. In FIG. 5 the results for two different standard SAP size distributions are presented. The SAP waste was collected and weighed below a normal suction drum during production for ten minutes per experiment. The core consisted of 18 g chemical pulp fibres and 12 g SAP and the line speed was 300 m/min. As expected the SAP waste increases when the pressure gradient decreases and/or the upper limit of the SAP particle diameter increases.

The invention claimed is:
1. An absorbent core for use in an absorbent product, the core after compression having a material density (based on the total content of the core) of at least 200 kg/m³, measured at a pressure of 0.5 kPa, wherein the absorbent core comprises three sub-layers, wherein a first sub-layer, viewed from a wearer-facing side of the core, primarily comprises pulp, the second sub-layer comprises SAP-particles and pulp, and the third sub-layer primarily comprises pulp, such that the composition of the second sub-layer is different than the composition of the first and third sub-layers, and at least 99.5% of the SAP-particles before compression have a maximum size of 300 µm.

2. The absorbent core according to claim 1, wherein the core is compressed during manufacturing.

3. The absorbent core according to claim 1, wherein the amount of SAP in the absorbent core is in the interval from 5 to 60%-weight of the absorbent core, based on the total weight of the core.

4. A method for manufacturing an absorbent core according to claim 1, comprising the steps of:
   a. forming an absorbent core in-line as a discrete or continuous core, wherein the core comprises three sub-layers, wherein a first sub-layer, viewed from the wearer-facing side of the core, primarily comprises pulp, a second sub-layer comprises the SAP-particles and pulp, and a third sub-layer primarily comprises pulp, such that the composition of the second sub-layer is different than the composition of the first and third sub-layers, wherein at least 99.5% of the SAP-particles before compression have a maximum size of 300 µm;
   b. compressing the absorbent core between compressing rollers so that the core after compression has a material density (based on the total content of the core) of at least 200 kg/m$^3$, measured at a pressure of 0.5 kPa; and
   c. providing a top sheet and a back sheet after compression, positioning the absorbent core between the top sheet and the back sheet, and sealing the product in order to provide a finished absorbent article.

5. The method according to claim 4, wherein the absorbent layer is formed in-line by air-laying absorbent core material on a mat-former.

6. The method according to claim 4, wherein the compression of the absorbent core is performed by (a) pre-compressing the core, and thereafter (b) compressing the core in one or two steps.

7. The method according to claim 6, wherein after pre-compression, two consecutive compression steps are performed, so that the outer part of the absorbent core is compressed in a first compression step, and the central part of the core is compressed in a second compression step.

8. The method according to claim 7, wherein the distance between the compression rollers is about 250 µm in the two consecutive compression steps.

9. The method according to claim 6, wherein a manufacturing rate of the absorbent core at one line is at least 300 m/min.

10. An absorbent product, selected from the group consisting of a sanitary napkin, a diaper, and an incontinence protection, comprising a top sheet, a back sheet and an absorbent core according to claim 1 between the top sheet and the back sheet.

11. The absorbent core according to claim 1, wherein the core after compression has a material density of at least 230 kg/m$^3$.

12. The absorbent core according to claim 3, wherein the amount of SAP in the absorbent core is in the interval from 10 to 50%-weight, based on the total weight of the core.

13. The method according to claim 4, wherein the core after compression has a material density of at least 230 kg/m$^3$.

14. The method according to claim 9, wherein the manufacturing rate is at least 500 m/min.

15. A method for manufacturing an absorbent core for use in an absorbent product, the core after compression having a material density (based on the total content of the core) of at least 200 kg/m$^3$, measured at a pressure of 0.5 kPa wherein the absorbent core has been formed in-line as a discrete or continuous core, wherein the absorbent core comprises SAP-particles, wherein at least 99.5% of the SAP-particles have a size of maximally 300 µm,
   comprising the steps of:
   a. forming an absorbent core in-line as a discrete or continuous core with three sub-layers, wherein a first sub-layer, viewed from the wearer-facing side of the core, primarily comprises pulp, a second sub-layer comprises the SAP-particles and pulp, and a third sub-layer primarily comprises pulp, such that the composition of the second sub-layer is different than the composition of the first and third sub-layers, wherein at least 99.5% of the SAP-particles before compression have a size of maximally 300 µm;
   b. compressing the absorbent core between compressing rollers so that the core after compression has a material density (based on the total content of the core) of at least 200 kg/m$^3$, measured at a pressure of 0.5 kPa; and
   c. optionally providing a top sheet and a back sheet after compression, positioning the absorbent core between the top sheet and the back sheet, and sealing the product in order to provide a finished absorbent article,
      wherein the compression of the absorbent core is performed by (a) pre-compressing the core, and thereafter (b) compressing the core in one or two steps.

16. The method according to claim 15, wherein after pre-compression, two consecutive compression steps are performed, so that the outer part of the absorbent core is compressed in a first compression step, and the central part of the core is compressed in a second compression step.

17. The method according to claim 15, wherein the distance between the compression rollers is about 250 µm in the two consecutive compression steps.

18. The method according to claim 15, wherein a manufacturing rate of the absorbent core at one line is at least 300 m/min.

19. The method according to claim 15, wherein a manufacturing rate is at least 500 m/min.

20. The absorbent core according to claim 1, wherein the first and third sub-layers are without SAP-particles.

* * * * *